(12) United States Patent
Kucklick

(10) Patent No.: US 11,759,582 B2
(45) Date of Patent: Sep. 19, 2023

(54) METHOD OF USING SEALANTS IN A GAS ARTHROSCOPY PROCEDURE

(71) Applicant: Cannuflow, Inc., Campbell, CA (US)

(72) Inventor: Theodore R. Kucklick, Campbell, CA (US)

(73) Assignee: Cannuflow, Inc., Campbell, CA (US)

( * ) Notice: Subject to any disclaimer, the term of this patent is extended or adjusted under 35 U.S.C. 154(b) by 808 days.

(21) Appl. No.: 16/412,263

(22) Filed: May 14, 2019

(65) Prior Publication Data

US 2019/0344022 A1    Nov. 14, 2019

Related U.S. Application Data

(60) Provisional application No. 62/671,303, filed on May 14, 2018.

(51) Int. Cl.
| | |
|---|---|
| A61M 13/00 | (2006.01) |
| A61B 18/20 | (2006.01) |
| A61B 18/00 | (2006.01) |

(52) U.S. Cl.
CPC .......... *A61M 13/003* (2013.01); *A61B 18/20* (2013.01); *A61B 2018/00565* (2013.01); *A61M 2210/02* (2013.01)

(58) Field of Classification Search
CPC ............ A61M 13/003; A61M 2210/02; A61M 11/02; A61B 18/20; A61B 2018/00565; A61B 17/3478; A61B 2017/3419; A61B 17/3474; A61B 1/317
See application file for complete search history.

(56) References Cited

U.S. PATENT DOCUMENTS

| | | | | |
|---|---|---|---|---|
| 5,720,894 | A * | 2/1998 | Neev ...................... | B23K 26/40 216/65 |
| 7,572,251 | B1 * | 8/2009 | Davison ............ | A61M 25/0133 604/500 |
| 2004/0018228 | A1 * | 1/2004 | Fischell ................. | A61K 47/14 424/78.22 |
| 2018/0092645 | A1 * | 4/2018 | Bonutti ............ | A61B 17/12136 |
| 2019/0125925 | A1 * | 5/2019 | Padua ..................... | A61L 15/28 |

FOREIGN PATENT DOCUMENTS

WO    WO-2004110512 A2 * 12/2004    ............. A61K 35/32

\* cited by examiner

*Primary Examiner* — James D Ponton
*Assistant Examiner* — Neeraja Gollamudi
(74) *Attorney, Agent, or Firm* — CROCKETT & CROCKETT, PC; K. David Crockett, Esq.; Niky Economy Syrengelas, Esq.

(57) ABSTRACT

A method of performing a gas arthroscopy by injecting a joint capsule with sealant prior to insufflation with gas. This sealant can be any biocompatible gel or liquid with sufficient viscosity or sealing capability to prevent air embolisms while performing gas arthroscopy.

14 Claims, 4 Drawing Sheets

METHOD OF USING SEALANTS IN A GAS ARTHROSCOPY PROCEDURE

This application claims priority to U.S. Provisional Patent Application 62/671,303 filed May 14, 2018.

FIELD OF THE INVENTIONS

The inventions described below relate to the field of gas arthroscopy.

BACKGROUND OF THE INVENTIONS

Arthroscopy of joints is a procedure performed nearly 8 million times per year and is done almost exclusively with fluid, particularly saline, to inflate a joint. (See R. T. Hegde, R. N. Avatgere; Air embolism during anesthesia for shoulder arthroscopy, BJA: British Journal of Anesthesia, Volume 85, Issue 6, 1 Dec. 2000, Pages 926-927.) Gas arthroscopy is not used because gas may travel along tissue planes and find its way into the venous system to cause embolisms or collect undesirably in locations distant from the surgical site. The problem with migration of gas from an arthroscopic joint space and the risks of air embolisms has previously been unsolved.

Gas arthroscopy has significant potential clinical utility for procedures where a fluid medium is undesirable, such as where surgical adhesives such as fibrin glues and cyanoacrylates are used, and other procedures where a wet environment inhibits adhesion or washes away the adhesive. The less desirable alternative to arthroscopy is an open procedure with the increased pain, scarring and recovery that goes with it.

SUMMARY

The methods described below make gas arthroscopy a safe alternative to an open procedure where a dry environment is required. The method involves the use of a surgical sealant to prevent gas leakage from the joint during the procedure. Flowable biocompatible surgical sealants such as polyethylene glycol (PEG), polyethyleneimine (PEI), fibrin, albumin, or gelatin are injected into an arthroscopic joint space before insufflation with gas.

A tourniquet system for gas arthroscopy may also be used to inhibit extravasation of gas from an arthroscopic joint space. The tourniquet or cuff that surrounds the joint may also be used for a variety of joints to squeeze the tissue around the joint and restrict perfusion into the area for hemostasis.

DETAILED DESCRIPTION OF THE INVENTIONS

Figure 1A:
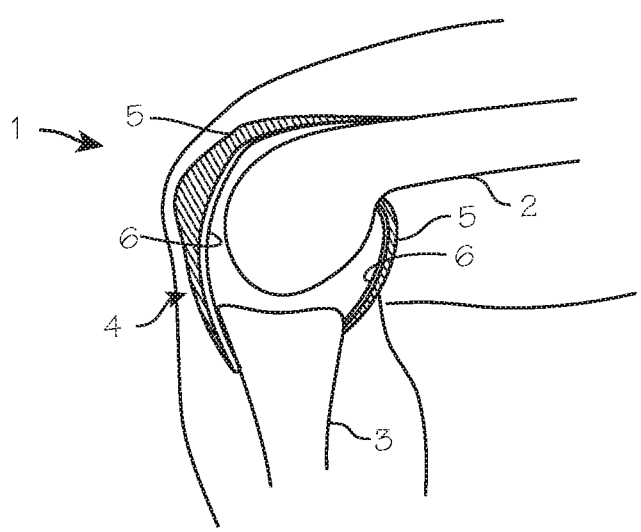
FIGS. 1a, 1b and 1c show a method of performing gas arthroscopy using a surgical sealant.
Figure 1B:
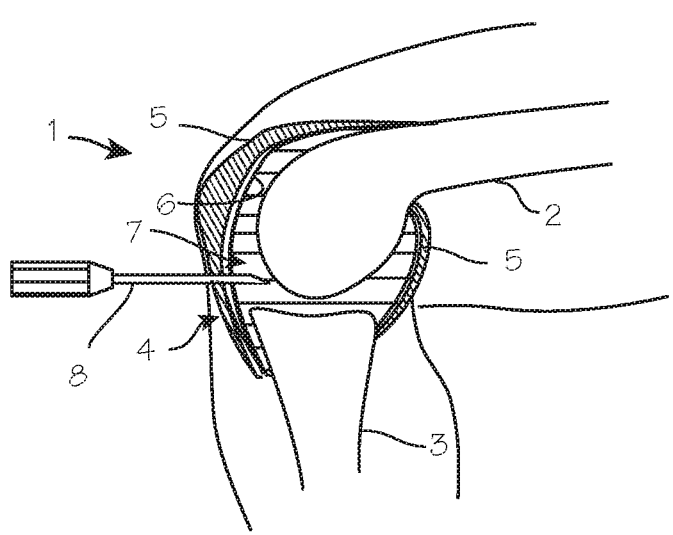
Figure 1C:
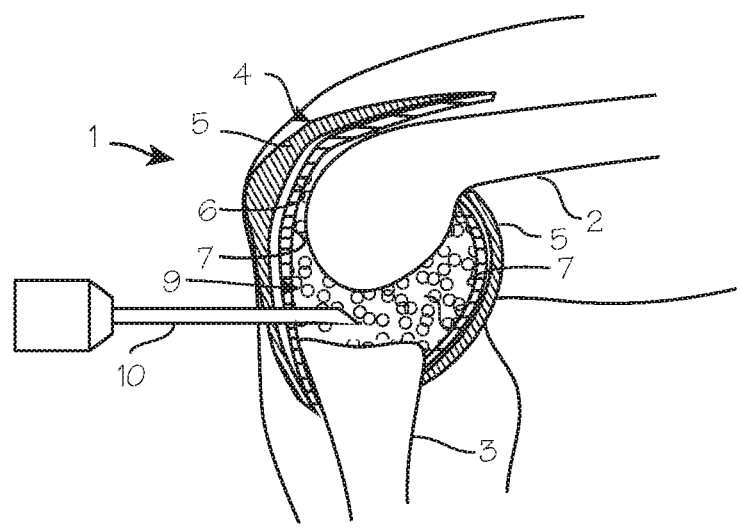

FIGS. 1a, 1b and 1c show a method of performing gas arthroscopy using a surgical sealant. Various anatomical landmarks in the patient's knee joint 1 are shown for reference, including the femur 2, the tibia 3, the joint capsule 4, the outer layer of the joint capsule 5 (i.e. the articular capsule), and the inner layer of the joint capsule 6 (i.e. the synovial membrane). FIG. 1a shows the knee joint prior to surgery. A sealant 7 is injected into the joint capsule 4 through a delivery device 8, as shown in FIG. 1b. The knee joint may be manipulated to distribute the sealant. Gas 9, such as filtered air or carbon dioxide, is then introduced into the joint capsule 4 through a gas delivery device 10, as shown in FIG. 1c, causing the joint capsule to be inflated with gas prior to an arthroscopic surgical procedure. The result is an expanded, insufflated joint capsule lined by a layer of sealant and filled with insufflated fluid (preferably gas).

Figure 2:
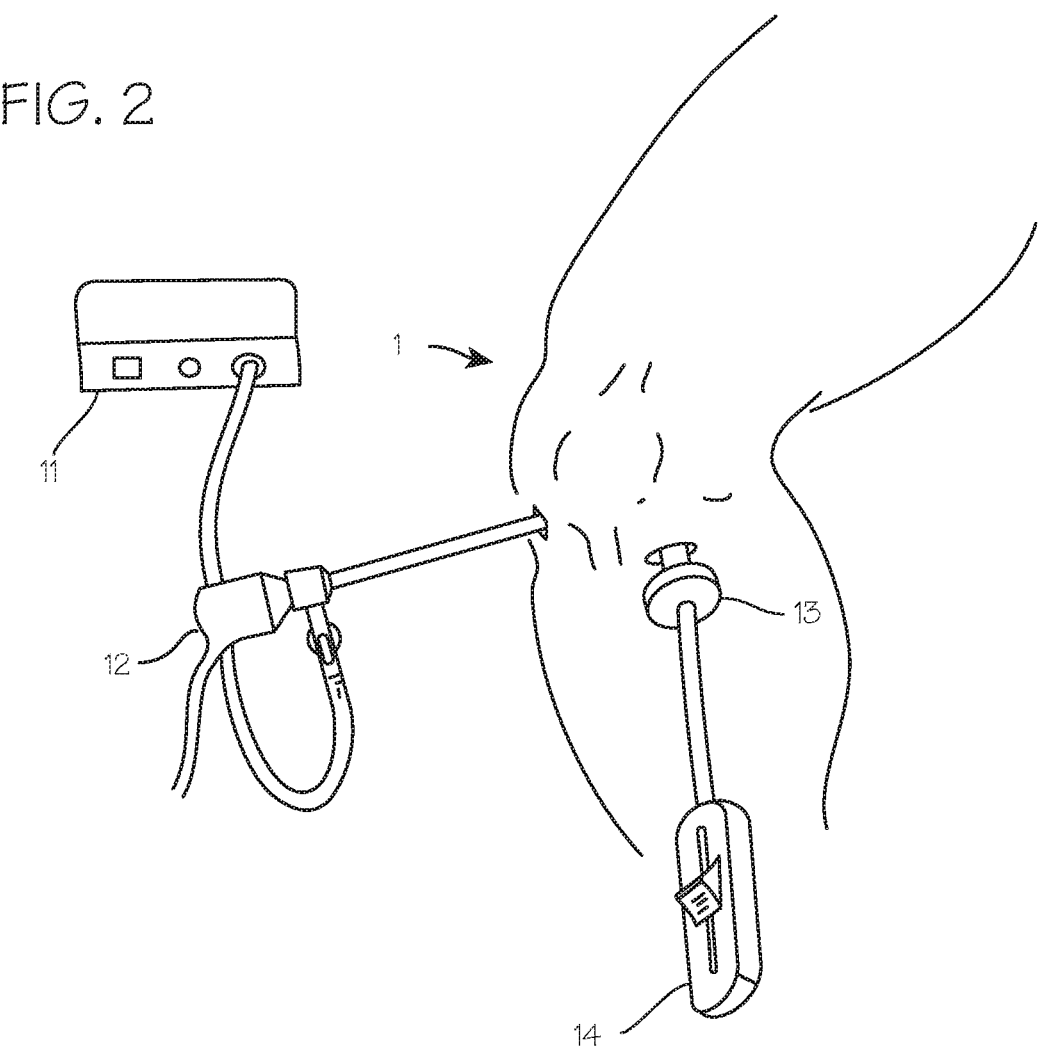
FIG. 2 shows a method of performing gas arthroscopy using a surgical sealant.

As shown in FIG. 2, gas is introduced into the knee joint, from an insufflator 11 through the gas delivery device, for example an arthroscope 12, causing the joint capsule 4 to be inflated with gas. During the surgical procedure the surgical sealant prevents the leakage of gas from the joint space into the surrounding tissue planes and vasculature. Upon completion of the surgical procedure, the gas is released, either by opening the valve on the arthroscope and letting it deflate, or by removal of the surgical instruments. A flexible gas sealing portal 13 may be used in conjunction with the biologic delivery device 14 to ensure that the joint stays properly inflated.

Various types of surgical sealants may be used, such as polyurethane, polyethylene glycol, polyvinyl alcohol, glucose, fibrin, gelatin, albumin, polysaccharides, chitosan, dextran, and chondroitin sulfate. A short acting sealant that dissolves and is absorbed without causing irritation to the joint would be most preferable. Chondroitin sulfate and other chemistry systems in this group are known to be biocompatible with joint tissue. Preferably the sealant would be of balanced viscosity to penetrate into the joint opening where gas would leak out, but stick to surfaces of the joint space. The sealant may be a gel, or a viscous liquid, or a lower viscosity fluid that may be cured if needed either by the mixing of the sealant with a static mixer before delivery, or with UV light. The sealant may also be loaded with anti-inflammatory medications such as steroids, anesthetics such as Marcaine, stem cells, or growth factors or other medications.

Though gas arthroscopy has been described, the method may be used in a liquid saline environment, for example for minimization of extravasation during arthroscopic surgery. The sealant would have to be biocompatible and not dissolve too quickly in water, for example PVA (polyvinyl alcohol) can be made water resistant.

Figure 3A:
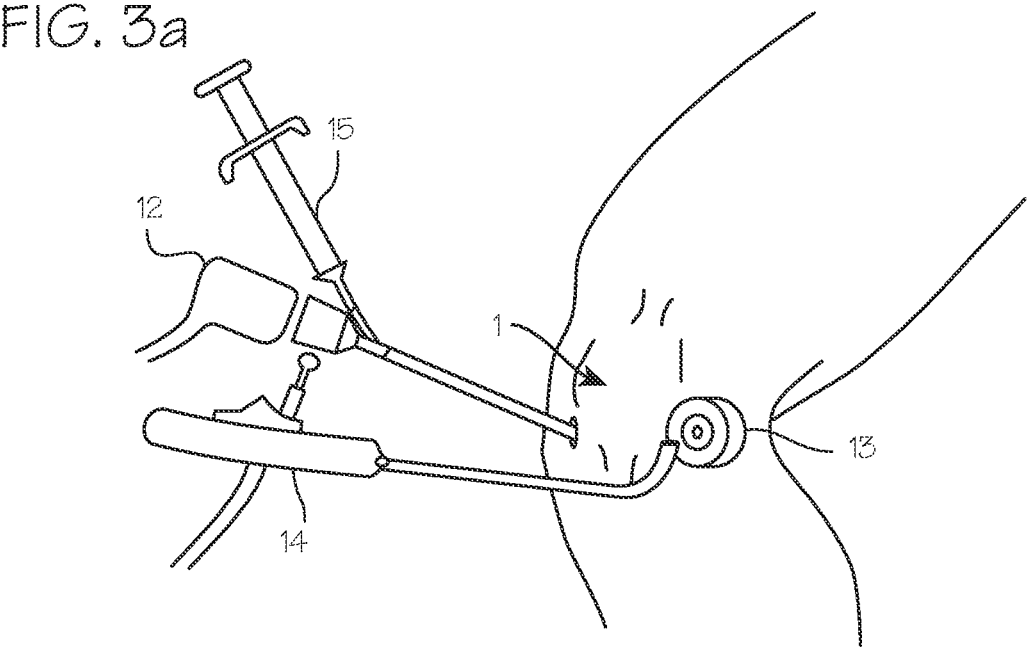
FIGS. 3a and 3b show a method of performing gas arthroscopy using a surgical sealant.
Figure 3B:
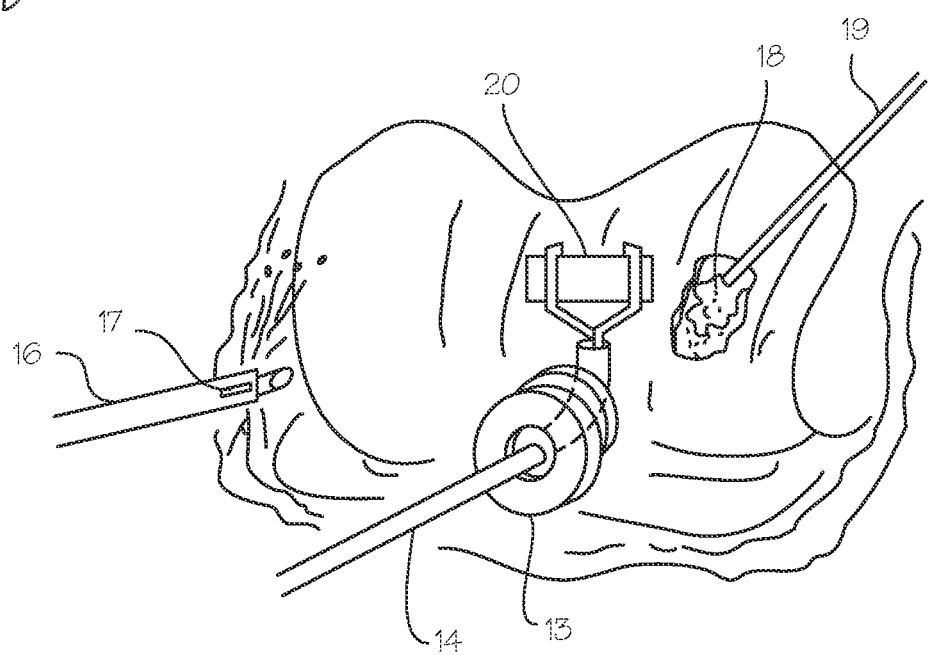

FIGS. 3a and 3b show a method of performing gas arthroscopy using a surgical sealant wherein the surgical sealant is distributed in the joint with a sprayer prior to or after the insufflation of the joint with gas. The sealant may be injected into the site via a syringe 15 and an arthroscopic instrument 12 with the capability of spraying the sealant in the surgical site. As shown in FIG. 3b, the distal end of the arthroscopic sheath 16 has an aperture 17 capable of spraying the sealant. The sprayer may be part of a coaxial sheath that is over an arthroscope, part of the arthroscope, or the sprayer can also be a separate device with a spray nozzle. A flexible gas sealing portal 13 may be used while a surgeon performs surgery on the joint with, for example, the biologic delivery device 14 to ensure that the joint stays properly inflated. A tissue adhesive 18 (e.g. fibrin glue) may be delivered through a fluid delivery device 19 to fix a biologic patch 20 in place during a biologic patch procedure.

In use, the surgeon injects the sealant into the knee joint and manipulates the joint to distribute the sealant. The sealant flows to fill holes, gaps and voids to form a barrier on the tissue defining the joint capsule. The joint space is inflated with gas. An arthroscope surgical procedure is performed. Upon completion of the procedure, the instruments are withdrawn and the gas escapes through the surgical portals.

Various medical procedures that are not possible in a liquid environment may be performed using this method. A gas-mediated procedure such as cartilage repair with a chopped cartilage conglomerate, biologic construct or cell-seeded membrane adhered in place with fibrin glue may be performed using a biologic delivery system. Ideally the use of fibrin glue is used in a gas environment rather than a saline environment since tissue adhesives do not adhere properly under water. The types of sheet biologics that can be delivered are: bioinductive collagen sheets for partial rotator cuff tears, structural patches for superior capsular reconstruction (SCR) procedures, and collagen construct sheets seeded with stem cells made by companies such as the MACI cartilage patch (Vericel, Ann Arbor Mich.) for repairing cartilage defects. Other procedures not possible in a liquid environment may be performed such as laser ablation of diseased cartilage and preparation of the implant site, or laser-based microfracture.

This dry arthroscopy system with a surgical sealant can facilitate a number of other procedures, such as delivery of bone cements for fracture repair, tacking down and repair of damaged cartilage and labral flaps, and repair of meniscal tears with adhesives instead of sutures. The system may also be used to repair partial rotator cuff tendon tears, and to adhere bioinductive repair constructs. The system and method may be used in other indications such as spinal procedures (where it is necessary to seal against cerebrospinal (CSF) fluid leaks), or neurosurgery where a sealed, dry surgical space needs to be created in a minimally-invasive way without an open surgical procedure. Another use for gas arthroscopy is when lasers are used that would otherwise be absorbed in a fluid medium (for example, use of a laser in a gas medium to perform microfracture is described in Kucklick, Method and Devices for Treating Damaged Articular Cartilage, U.S. Publ. No. 2009/0105792A1).

Figure 4A:
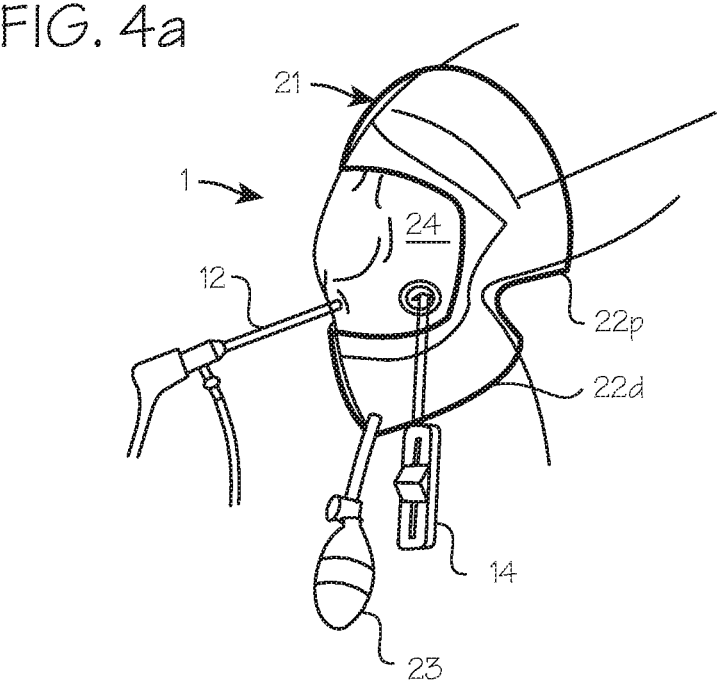
FIGS. 4a and 4b shows a tourniquet system for use during gas arthroscopy to prevent extravasation of gas into tissue.
Figure 4B:
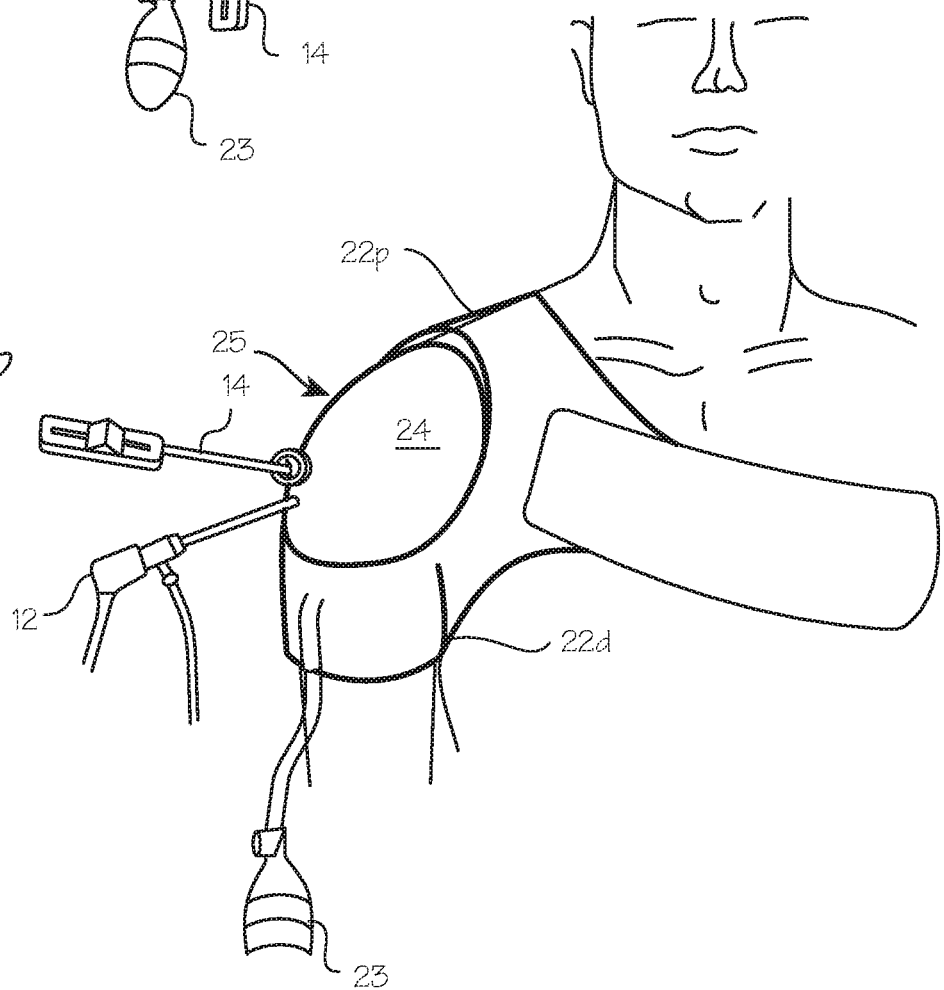

FIGS. 4a and 4b illustrate a tourniquet system 21 for gas arthroscopy to prevent the spread of insufflation gas into the surrounding tissue (extravasation) and to keep it confined to the joint. This is a circumferential tourniquet wrap 22, having a proximal tourniquet 22p, a distal tourniquet 22d, and an aperture. The tourniquet is configured to be placed around the joint 1, to provide circumferential compression around the joint, and keep the gas in the joint and limit travel of any gas which enters the blood vessels around the joint. This prevents unwanted tissue dissection, air embolisms, and interstitial air pockets. The tourniquet wrap compresses closely to the joint to prevent unwanted subcutaneous emphysema in the soft tissue between the tourniquet wrap and the joint. FIG. 4a shows a tourniquet system in a knee surgery, including the arthroscope 12, biologic delivery device 14, and bulb 23. FIG. 4b shows a tourniquet system in a shoulder surgery. The tourniquet wrap is placed around the shoulder joint 24 and inflated to cause circumferential compression around the joint. Gas is introduced into the joint capsule via an arthroscopic instrument. A surgical procedure is then performed. Upon completion of the surgical procedure, the gas is withdrawn, the tourniquet wrap deflated and removed. Generally, use of the tourniquet wrap in a method of performing arthroscopic surgery comprises the steps of constricting an area proximal to a joint with a tourniquet, constricting an area distal to the joint with a tourniquet, insufflating the joint with fluid, and performing an arthroscopic surgical procedure on the joint.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. A method of performing dry gas arthroscopy using a surgical sealant, the method comprising:
   injecting a dissolvable viscous gel surgical sealant into a joint capsule through a delivery device;
   insufflating the joint capsule with gas;
   performing an arthroscopic surgical procedure; and
   upon completion of the arthroscopic surgical procedure, allowing the gas to escape from the joint capsule.

2. The method of claim 1 where the sealant is a flowable biocompatible surgical sealant.

3. The method of claim 1 where the joint capsule is within a knee joint.

4. The method of claim 1 where the arthroscopic surgical procedure is a laser surgery.

5. The method of claim 1 wherein the step of insufflating is performed after the step of injecting.

6. The method of claim 1 wherein the step of insufflating is performed before the step of injecting.

7. The method of claim 1 wherein the step of insufflating is performed simultaneously with the step of injecting.

8. A method of performing dry gas arthroscopy using a surgical sealant, said method comprising:
   injecting a dissolvable viscous gel surgical sealant into a joint capsule with an arthroscopic instrument, said arthroscopic instrument further comprising a sprayer disposed at a distal end of the arthroscopic instrument;
   spraying the sealant in the joint capsule;
   insufflating the joint capsule prior to an arthroscopic surgical procedure;
   performing the arthroscopic surgical procedure; and
   upon completion of the arthroscopic surgical procedure, allowing a gas to escape from the joint capsule.

9. The method of claim 8 wherein the sprayer comprises an aperture at the distal end of the arthroscopic instrument.

10. The method of claim 8 further comprising a sheath disposed over the arthroscopic instrument, wherein the sprayer comprises an aperture at a distal end of the sheath.

11. The method of claim 8 where the joint capsule is within a knee joint.

12. The method of claim 8 wherein the step of insufflating is performed after the step of injecting.

13. The method of claim 8 wherein the step of insufflating is performed before the step of injecting.

14. The method of claim 8 wherein the step of insufflating is performed simultaneously with the step of injecting.

* * * * *